(12) United States Patent
Doubler et al.

(10) Patent No.: US 9,615,862 B1
(45) Date of Patent: Apr. 11, 2017

(54) MODULAR HEAD INSERTER

(71) Applicant: Spinal LLC, Palm Beach Gardens, FL (US)

(72) Inventors: Robert L. Doubler, Monroe, MI (US); John E. Hammill, Sr., Maumee, OH (US)

(73) Assignee: Spinal LLC, Palm Beach Gardens, FL (US)

( * ) Notice: Subject to any disclaimer, the term of this patent is extended or adjusted under 35 U.S.C. 154(b) by 0 days.

(21) Appl. No.: 14/947,330

(22) Filed: Nov. 20, 2015

(51) Int. Cl.
*A61B 17/58* (2006.01)
*A61B 17/70* (2006.01)

(52) U.S. Cl.
CPC ................................ *A61B 17/7076* (2013.01)

(58) Field of Classification Search
CPC ............ A61B 17/7034; A61B 17/7035; A61B 17/7037; A61B 17/7074; A61B 17/7076; A61B 17/7082; A61B 17/8875
See application file for complete search history.

(56) References Cited

U.S. PATENT DOCUMENTS

| | | |
|---|---|---|
| 5,545,165 A | 8/1996 | Biedermann et al. |
| 5,584,834 A | 12/1996 | Errico et al. |
| 5,628,740 A | 5/1997 | Mullane |
| 5,725,527 A | 3/1998 | Biedermann et al. |
| 5,879,350 A | 3/1999 | Sherman et al. |
| 6,050,997 A | 4/2000 | Mullane |
| RE37,665 E | 4/2002 | Ralph et al. |
| 6,371,957 B1 | 4/2002 | Amrein et al. |
| 6,478,798 B1 | 11/2002 | Howland |
| 6,565,565 B1 | 5/2003 | Yuan et al. |
| 6,610,062 B2 | 8/2003 | Noblitt et al. |
| 6,610,063 B2 | 8/2003 | Kumar et al. |
| 6,613,050 B1 | 9/2003 | Wagner et al. |
| 6,626,906 B1 | 9/2003 | Young |
| 7,105,029 B2 | 9/2006 | Doubler et al. |
| 7,118,303 B2 | 10/2006 | Doubler et al. |
| 7,334,961 B2 | 2/2008 | Doubler et al. |
| 7,335,201 B2 | 2/2008 | Doubler et al. |
| 7,438,715 B2 | 10/2008 | Doubler et al. |
| 7,658,582 B2 | 2/2010 | Doubler et al. |
| 7,678,138 B2 | 3/2010 | Fitts et al. |
| 7,862,281 B2 | 1/2011 | Doubler et al. |
| 7,981,143 B2 | 7/2011 | Doubler et al. |
| RE42,715 E | 9/2011 | Sones |
| 2008/0243133 A1* | 10/2008 | Heinz .................. B25B 23/101 606/104 |

* cited by examiner

*Primary Examiner* — Ellen C Hammond
(74) *Attorney, Agent, or Firm* — McHale & Slavin, P.A.

(57) ABSTRACT

Disclosed is an instrument to assist in installing bottom loading orthopedic devices. The orthopedic devices are used to fix and stabilize bones to correct anomalies in skeletal structure occurring naturally or by trauma. Bone screws are anchored and tulips by the disclosed instrument wherein push/pull forces are equalized to eliminate the imposition of stress on the skeletal of individual.

8 Claims, 14 Drawing Sheets

MODULAR HEAD INSERTER

CROSS REFERENCE TO RELATED APPLICATIONS

This patent application is related to U.S. patent application Ser. No. 14/643,448, the contents of which are incorporated herein by reference.

FIELD OF THE INVENTION

This invention relates to orthopedic surgery and, in particular, to an instrument for securing a modular head assembly.

BACKGROUND OF THE INVENTION

Chronic back problems are caused by intervertebral disc disease and deterioration and loss of stability of the intervertebral joints. Examples of these spinal conditions include degenerative disc disease, scoliosis, spondylolisthesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized. Severe trauma to the back can further cause conditions wherein the spine needs to be stabilized. There are many instances in which it is necessary to stabilize and fix bones and bone fragments in a particular spatial relationship to correct the location of skeletal components due to injury or disease. One group of devices employ a number of bone screws placed across a discontinuity in adjacent vertebrae and connected by a rod to maintain a predetermined spatial location.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050; 6,371,957; 6,050,997; 5,879,350; 5,725,527; 5,628,740; and 5,545,165, the disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

The inventors implants includes U.S. Pat. Nos. 7,105,029; 7,118,303; 7,334,961; 7,335,201; 7,438,715; 7,658,582; 7,678,138; 7,862,281; 7,981,143 and RE42,715, the disclosures of which are incorporated herein by reference. In normal practice a screw and modular head are assembled in a factory before being anchored to a bone. Alternatively a screw is anchored to the bone and the modular head then secured to the screw. The modular heads, which are commonly referred to as a tulip, are then connected together by a rod having sufficient stiffness to maintain the desired skeletal orientation. The problem with mounting a tulip onto a bone screw is the pressure necessary during the installation step. Thus, what is needed in the art is an instrument to mount a tulip to an anchored bone screw wherein the instrument has a force canceling effect.

SUMMARY OF THE INVENTION

An instrument to assist in installing orthopedic devices used to fix and stabilize bones to correct anomalies in skeletal structure occurring naturally or by trauma. Bone screws are anchored into bones and a module head, commonly referred to as a tulip, is attached to the anchored bone screw by use of the instant instrument wherein push/pull forces are equalized.

The instrument works with bone screws that have an internal relief groove added to the shank. The instrument is first loaded with a tulip wherein grip fingers hold the tulip in a mounting position. A tip of the instrument includes a collet that protrudes through the tulip. The collet is sized for insertion into the shank of the bone screw and includes an expanding pin to expand the collet into a relief groove located in the shank thereby securing the instrument to the bone screw. In operation, a handle of the instrument is squeezed about 5° of motion for control of the expanding collet tip by pushing an expander pin forward to block the collet area from collapsing thereby locking the instrument tip on to shank. The handle is then squeezed about 20° wherein a cam controls a push sleeve which pushes on the tulip at the same time the collet pulls on the bone screw in equal force but opposite direction wherein the shank head is captured by the tulip. As the handle is squeezed about 5° further, lever handle fully cycled, the cam controlling the collet pulls the expander pin back which unblocks the collet area so that the collet tip collapses and can be removed from the shank.

An objective of the invention is to provide a modular head (tulip) inserter that can cancel out forces necessary when installing tulip on an anchored bone screw using a PUSH-PULL design.

Another objective of the invention is to provide an instrument capable of holding a tulip in position for mounting to a bone screw.

Still another objective of the invention is to provide a modular head inserter permitting one handed use.

Another objective of the invention is to provide a modular head inserter having a single stroke lever handle to capture the shank head, mount the tulip, and disengage from the bone screw.

Yet still objective of the invention is to provide a modular head inserter with cam type motion control.

Other objectives and further advantages and benefits associated with this invention will be apparent to those skilled in the art from the description, examples and claims which follow.

DETAILED DESCRIPTION OF THE PREFERRED EMBODIMENT

Detailed embodiments of the instant invention are disclosed herein; however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Figure 1:
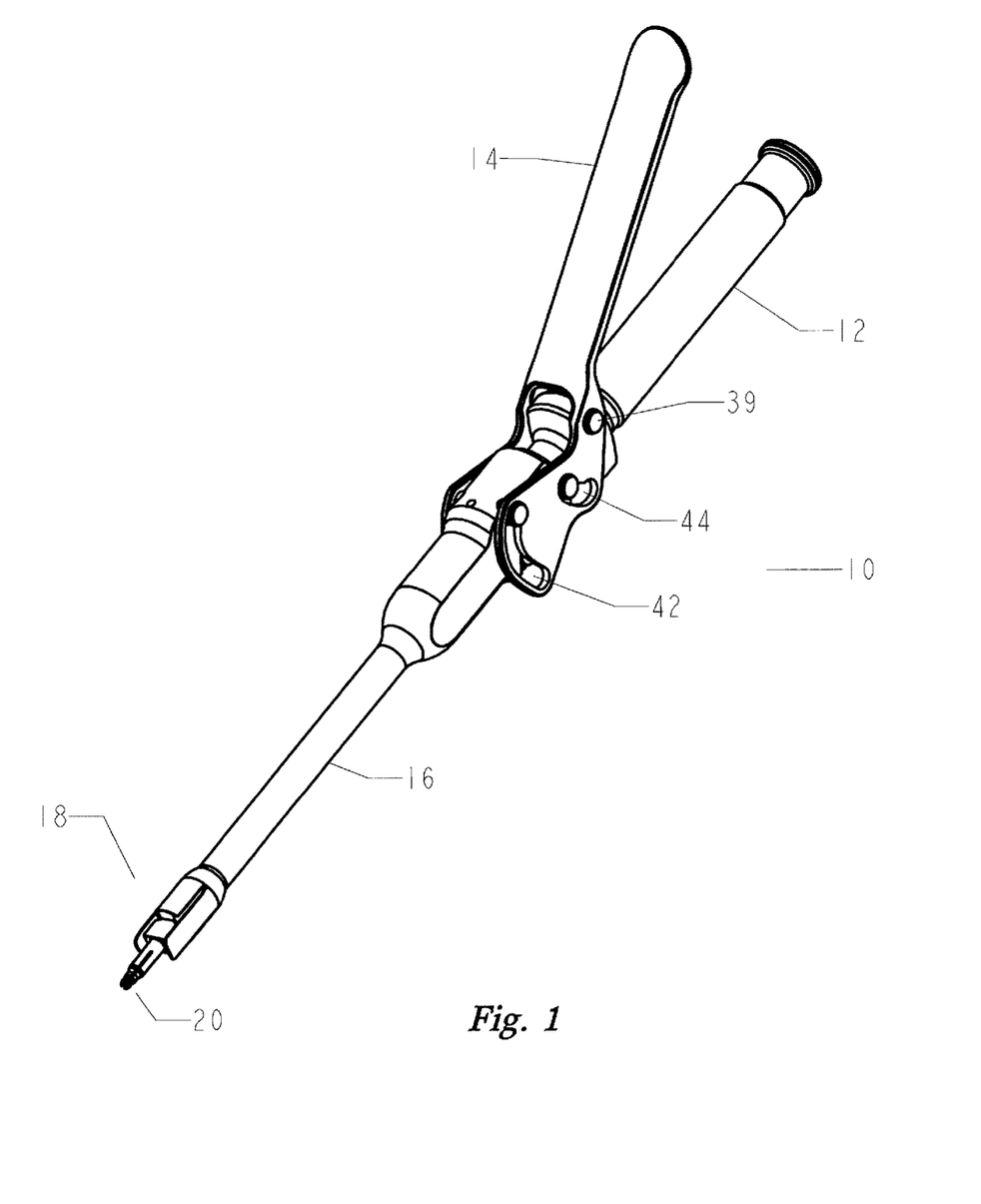
FIG. 1 is an isometric view of the modular head inserter.
Figure 2:
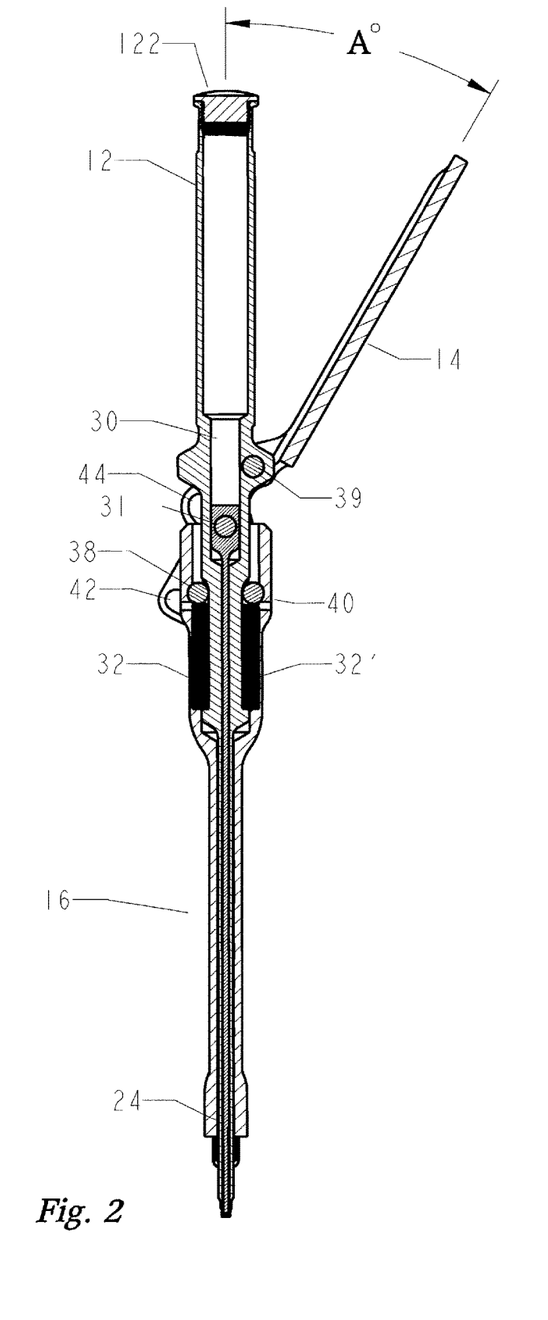
FIG. 2 is a cross-sectional view thereof.
Figure 3:
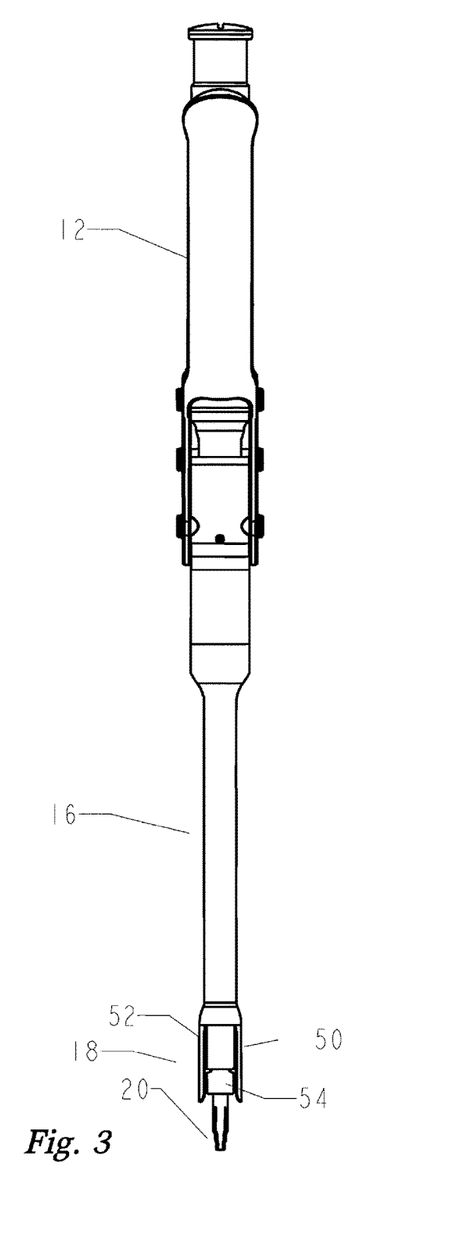
FIG. 3 is a right side view thereof.
Figure 4:
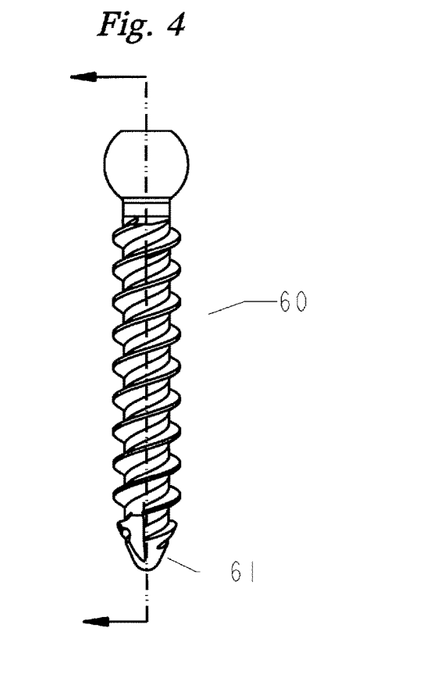
FIG. 4 is a front view of a bone screw shank portion.
Figure 5:
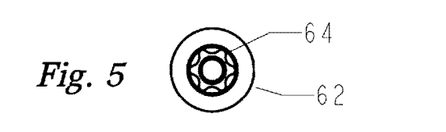
FIG. 5 is a top view of a bone screw.
Figure 6:
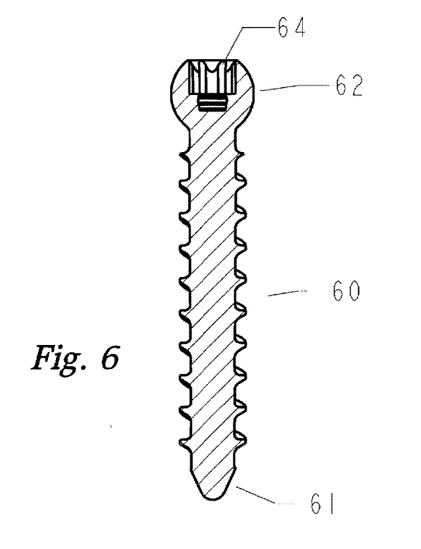
FIG. 6 is a cross-sectional view of a bone screw.
Figure 7:
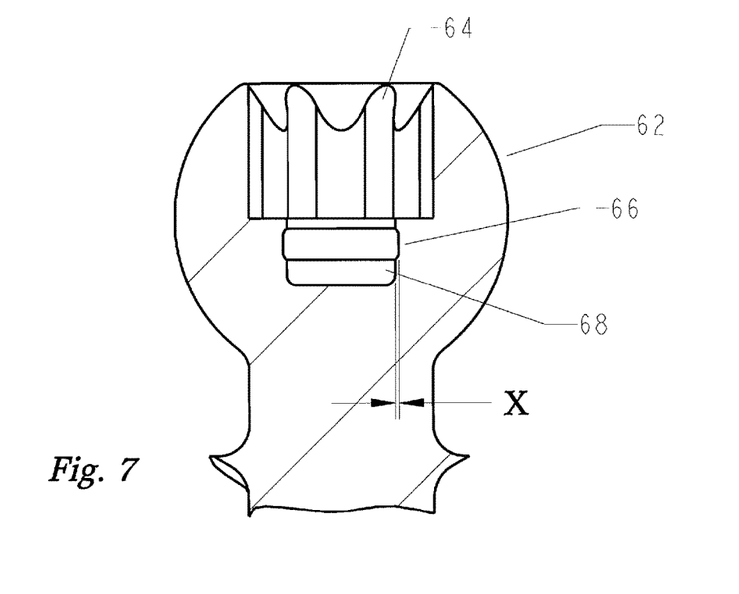
FIG. 7 is an enlarged view of the head of a bone screw showing a radial relief grip groove.
Figure 8:
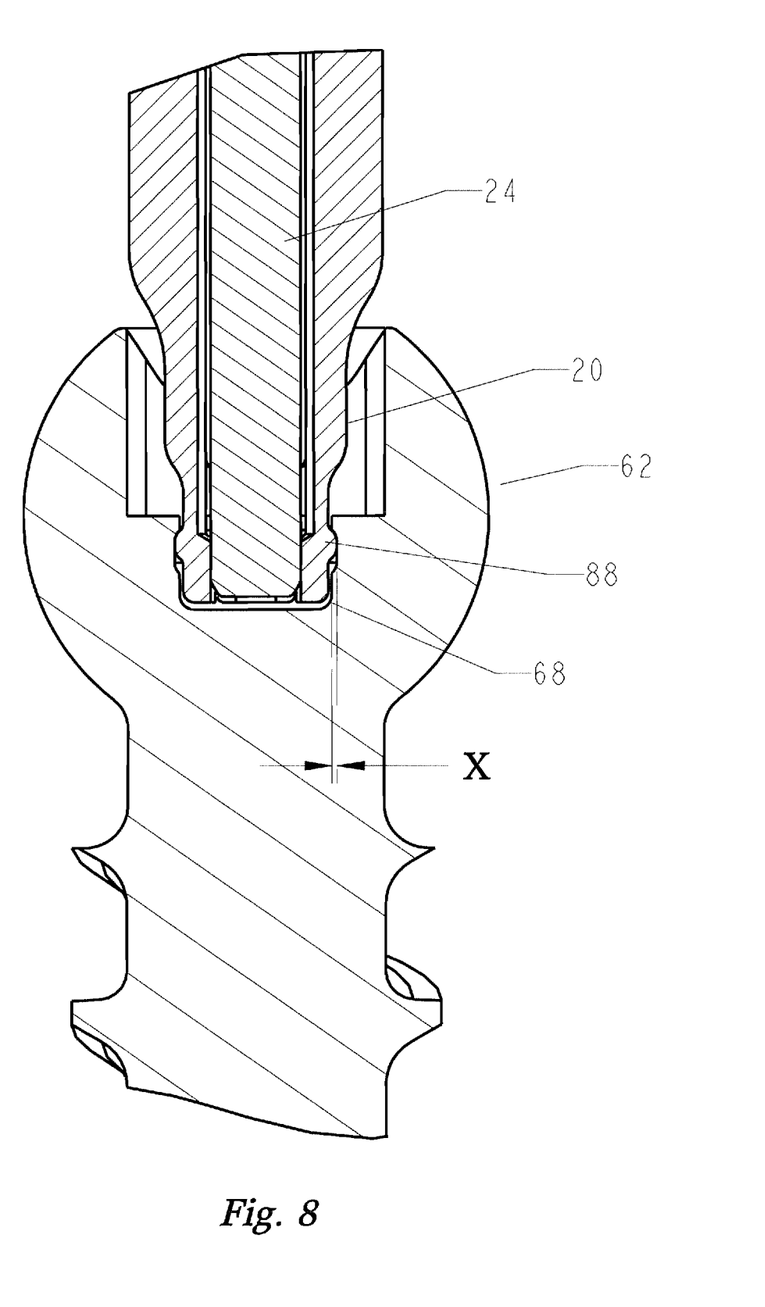
FIG. 8 is an enlarged view of the head of a bone screw with a collet tip inserted and expander pin deployed.

Referring to FIGS. 1-3, set forth is the modular head inserter instrument 10, having a body 12 with a lever handle 14 and push sleeve 16. At a distal end 18 of the push sleeve 16 is a collet tip 20 used for temporary coupling to a relieve groove in a bone screw. The push sleeve 16 houses an expander pin 24 for insertion through the collet tip 20. The collet tip 20 is driven by the expander pin head 110 that can slide within the cavity passageway 30. The expander pin head 110 includes an aperture 114 for receipt of cam pin 31. The cam pin 31 is operatively associated with lever handle 14 for movement of expander pin 24. Upon movement of the lever handle 14, the cam pin 31 travels within cam track 44 causing the expander pin 24 to extend into the collet tip 20. To provide an equal push/pull action, the body 12 which forms the collet tip 20 is pulled back at the same time the expander pin 24 is moved. The springs 32 and 32' are compressed to provide a bias against the lever handle 14 movement. The lever handle 14 operating in conjunction with cam track 44 to operate the expander pin 24 and body 12 movement. The body 12 is attached to the push sleeve 16 with attachment pin 38. The cam track 44 is operated in conjunction with cam pin 40, wherein the cam track 44 is pivoted along pivot pin 39 for pushing of the push sleeve 16 through cam pin 40, while cam track 44 is operated in conjunction with cam pin 31 for pulling of the inserter pin 24.

Referring to FIGS. 4 through 8, the shank 61 of a screw 60 includes a head 62 with a Hexalobe drive receptacle 64 used for rotation of the screw 60 for installation into a bone. Along the bottom of the receptacle 64 is a cavity 68 having a relief groove 66. The relief groove 66 is larger than the diameter of the cavity 68 by a distance X. The relief groove 66 is sized to receive lobe 88 when the expander pin 24 causes the tip section of the collet to expand. Once the lobe 88 of the collet tip 20 is expanded into the relief groove 66, the screw 60 is temporarily secured to the instrument. Insertion of the collet tip 20 and expansion by the expander pin 24 secures the instrument to the screw 60, which allows a "pull" against Hexalobe drive feature of the shank head 62 while the push sleeve engages the tulip 80.

Figure 9:
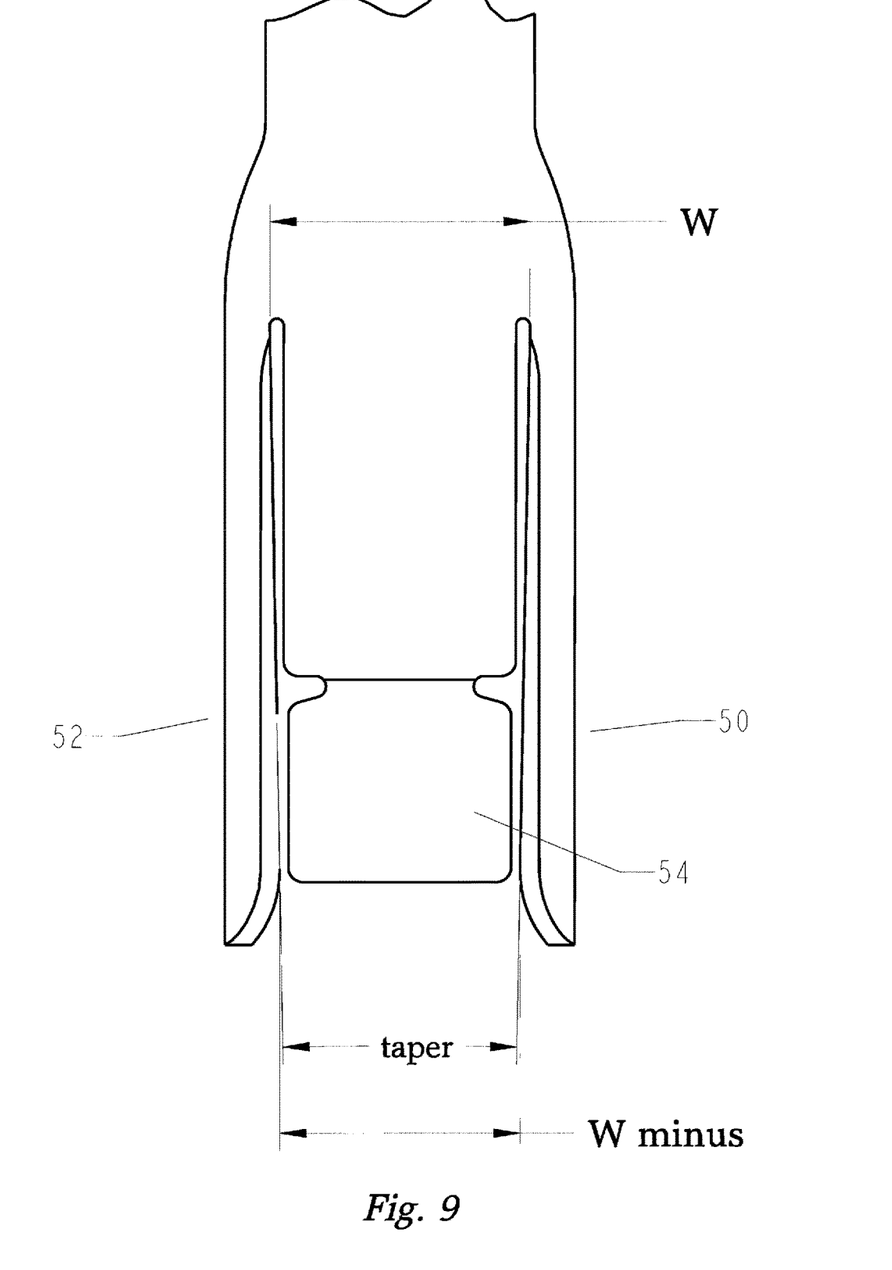
FIG. 9 is a front view of the tip end of a push sleeve illustrating a modular head nest area and pinch fingers.
Figure 10:
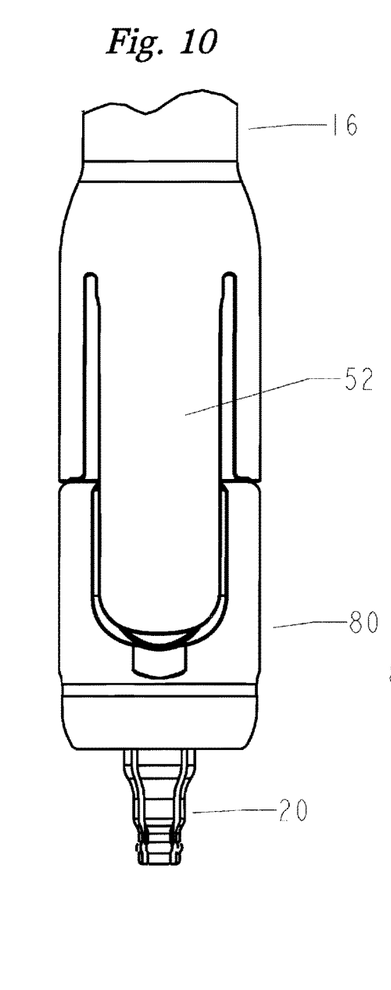
FIG. 10 is a side view of the collet tip.

The distal end 18 of the push sleeve 16 includes pinch fingers 50 and 52 to provide frictional engagement for securing a tulip 80 to the instrument during a preloading step. Referring to FIG. 9, the pinch fingers are formed integral to the push sleeve 16 with a width W that allows the edges of a tulip to be pinched providing a temporary securement to the instrument. The spacing between the rest area 54, 55 and the pinch fingers 50 and 52 is tapered to allow ease of mounting the tulip 80 to the push sleeve 16. As the tulip 80 is being pushed onto the push sleeve 16, the pinch fingers 50 and 52 provide an increasing tightened grip on the tulip 80. As further illustrated in FIGS. 10 and 11, pinch finger 52 is illustrated capturing tulip 80, the finger 52 providing a biasing force and frictional engagement against an edge 81 formed by the U-shaped opening of tulip 80. The upper edge 83 of the tulip 80 is flush against a lower edge 85 of the push sleeve 16. The tulip rest area 54 and 55 are configured to the U-shaped opening of a tulip for maintaining the tulip in position during the installation step.

Figure 11:
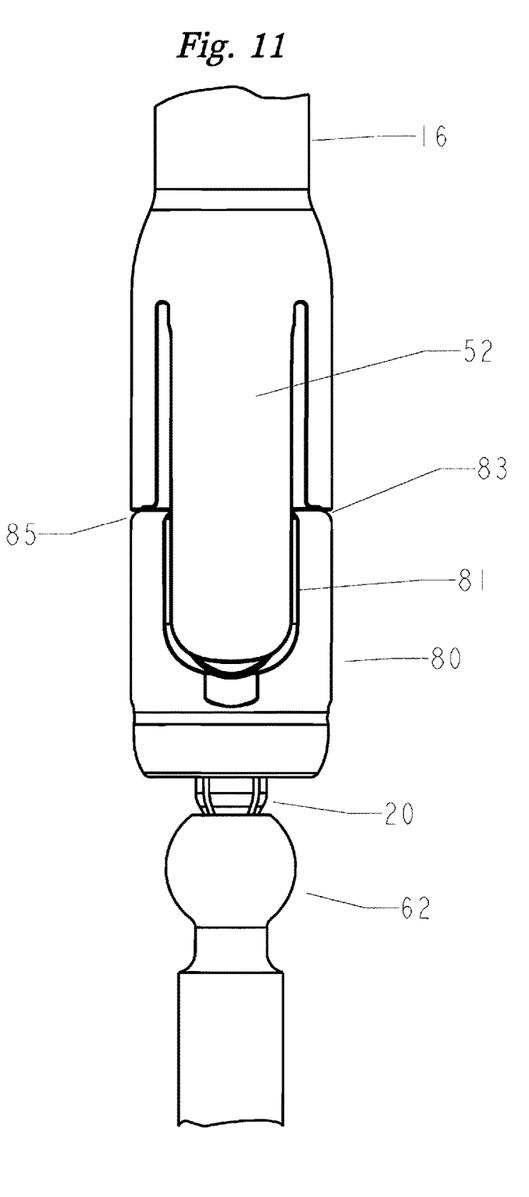
FIG. 11 is a side view of the inserter tip fully inserted into a bone shank.
Figure 12:
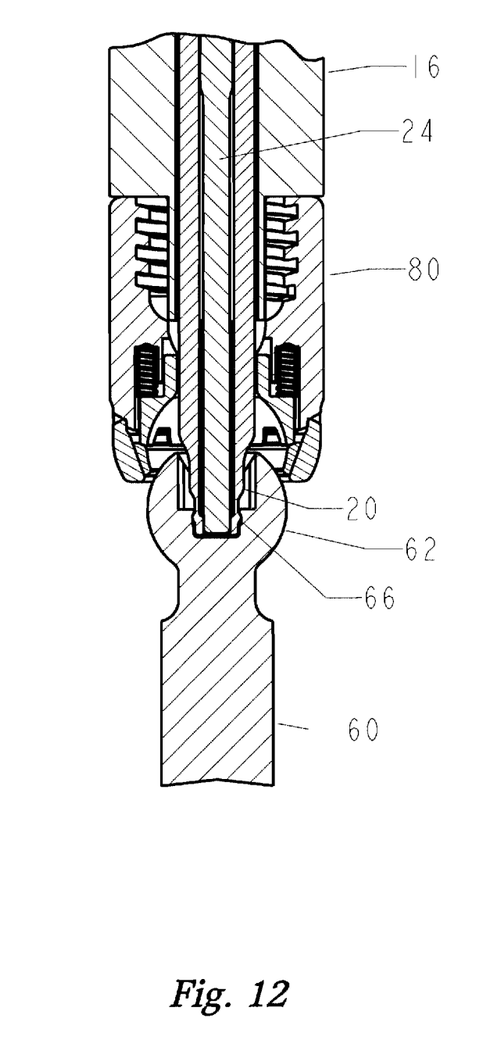
FIG. 12 is a cross-sectional view of the inserter tip shown with expander pin deployed.
Figure 13:
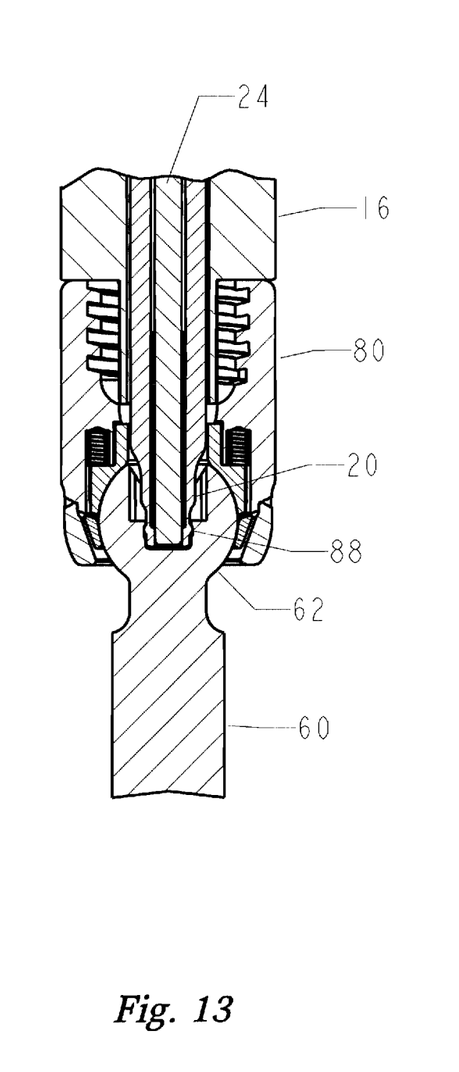
FIG. 13 is a cross-sectional view of the inserter tip with push sleeve fully deployed and capturing a bone screw.
Figure 14:
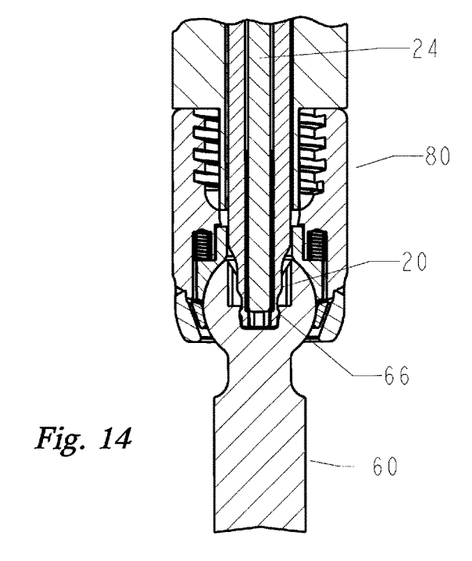
FIG. 14 is a cross-sectional view of the inserter tip shown with expander pin pulled back.

FIG. 12 is a cross-sectional view of FIG. 11, further depicting the collet tip 20 within the cavity 68 of the screw 60, with the expander pin 24 expanding the collet 20 causing the lobe 88 to fit within the relief groove 66. The pinch fingers 50 and 52 hold the tulip 80 in position during the installation steps. Referring to FIG. 13, as the collet tip 20 is pulled upward, the push sleeve 16 pushes downward providing a cancelling of forces wherein attachment of the tulip 80 to the screw 60 places no pressure on the skeletal of the body. FIG. illustrates the collet tip 20 with the expander pin 24 partially withdrawn so as to collapse the collet tip 20 for removal from the cavity 68. The tulip 80, is a bottom loading tulip which is secured to an anchored screw 60.

Figure 15:
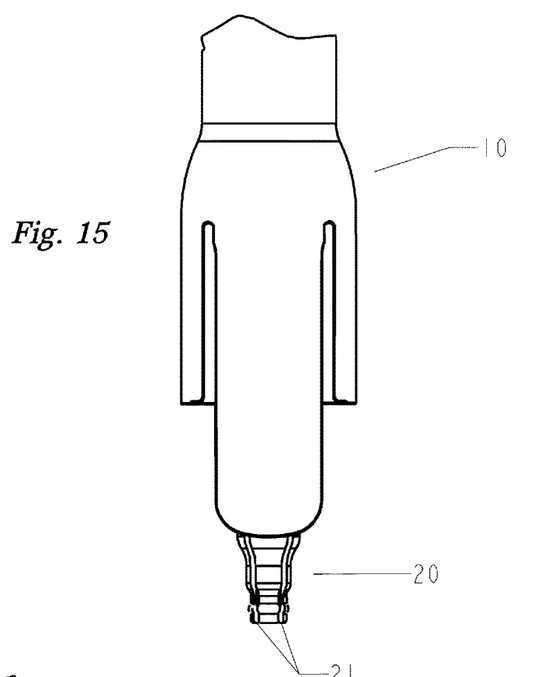
FIG. 15 is a plane view of inserted tip collapsed.
Figure 20:
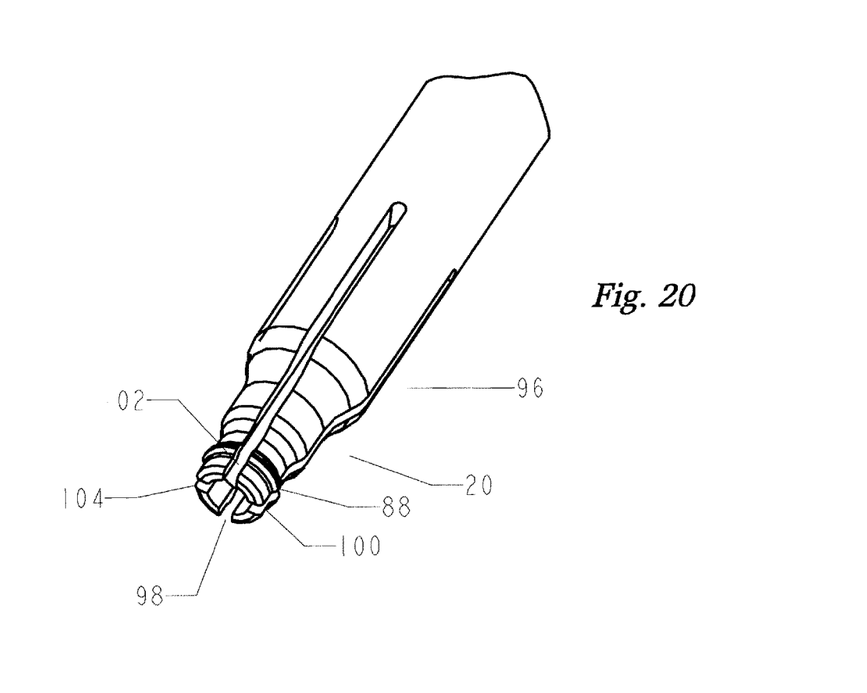
FIG. 20 is an enlarged view of the collet.

FIG. 15 illustrates the inserter instrument 10 removed from the tulip 80 wherein the collet tip 20 is relaxed and the expander pin 24 has been withdrawn. The collet tip 20 includes spaces 21 formed by removed material that allows for the diameter of the collet to be reduced in size when the expander pin is removed to allow for ease of inserting into a screw or removal therefrom. Further, the diameter of the collet can be expanded in diameter wherein the lobe 88 may engage the relief groove 66 when the expander pin 24 is inserted. FIG. 20 illustrates the distal end 96 of the collet tip 20 with the spaces 98, 100, 102, and 104 providing relief around the diameter of the collet tip 20 to allow for the expansion and contraction of the collet tip 20 based upon the position of the expander pin 24. The spaces consist of removed material along a line parallel to a central axis of the collet. The spaces may consist of one or more to allow for expansion and contraction. The expander pin 24 being inserted into the collet tip 20 causes the expansion wherein lobe 88 will conform to the relief groove 66 of the shank head 62. Removal of the expander pin 24 allows the collet tip 20 to collapse along the spaces providing a relief line for reducing the diameter of the collet.

Figure 16:
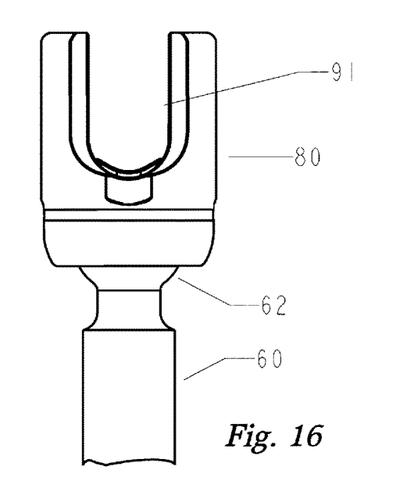
FIG. 16 is a plane view of an assembled modular head.

FIG. 16 illustrates the tulip 80 attached to the head 62 of the screw 60. In this position the screw 60 is anchored to the bone and the tulip 80 is securely attached to the screw 60, the installation of the tulip 80 did not require any pressure being applied to the bone. The tulip 80 has a U-shaped receptacle 91 for receipt of a connecting rod, not shown, for securing to adjoining modular screw head assemblies.

Figure 17:
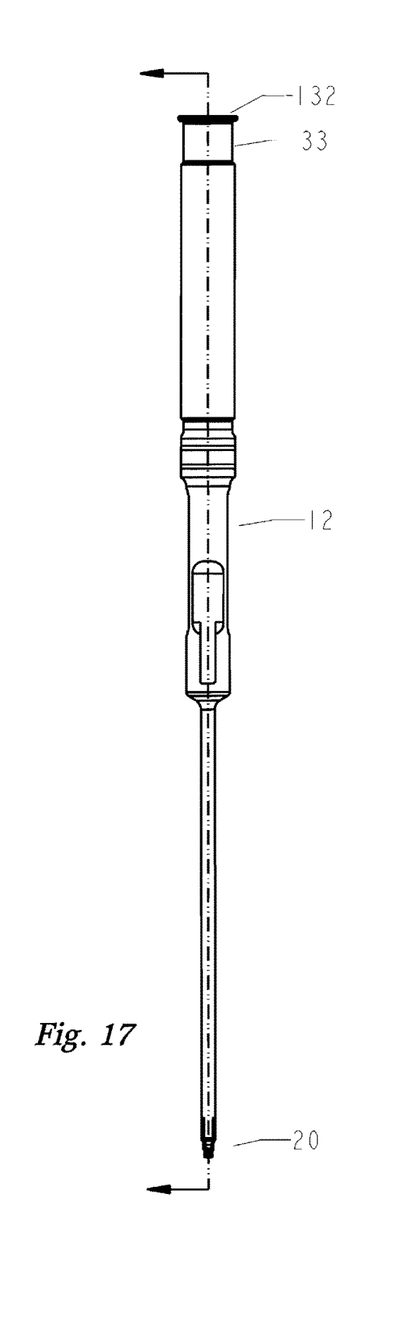
FIG. 17 is a plane view of the body element.
Figure 18:
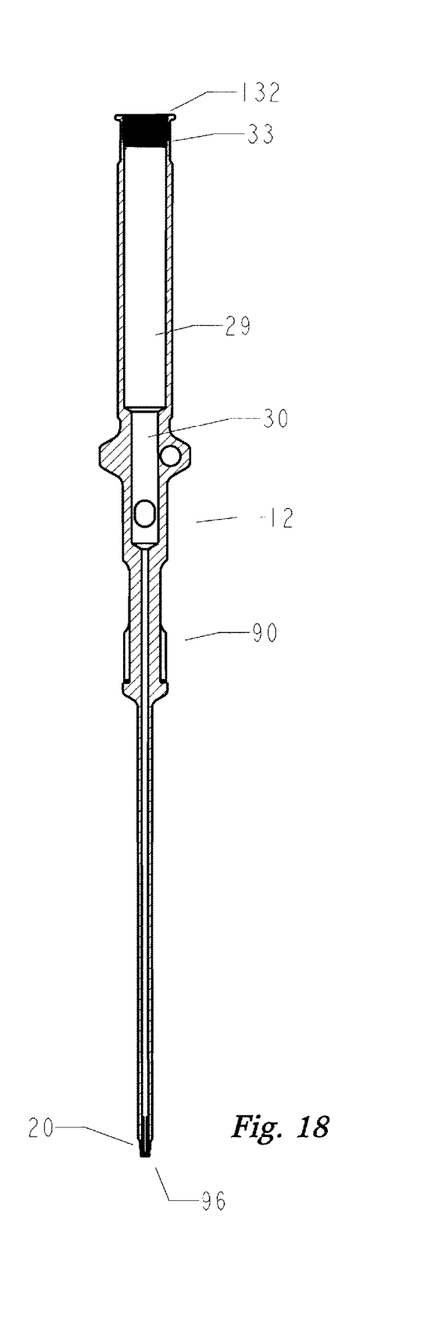
FIG. 18 is a cross-sectional view of FIG. 17.
Figure 19:
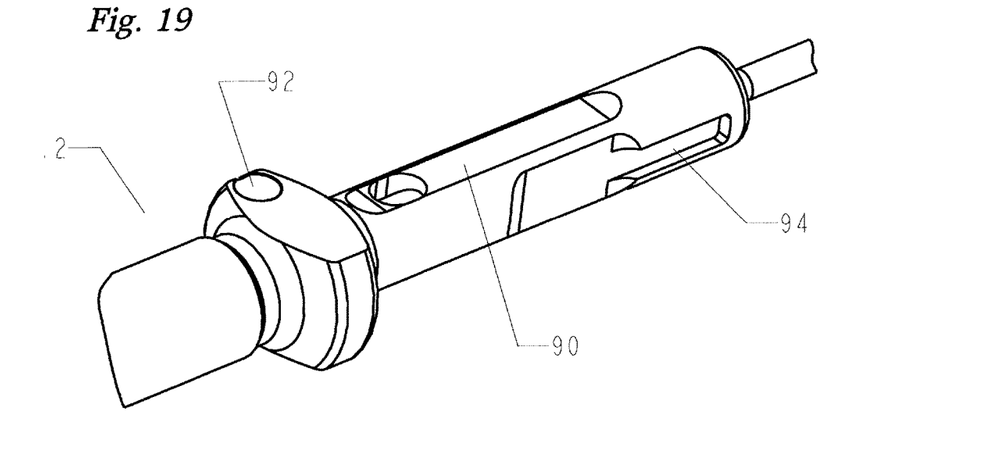
FIG. 19 is an enlarged isometric mid-section view of the body element.

FIG. 17 and FIG. 18 illustrates the body element 12 formed from a unitary piece of material having the collet tip 20 formed along one end and a passageway 30 for receipt of the head of the expander pin 24. The passageway 30 is accessed by use of access opening 29 formed at the proximal end of the body element 12. A cap 132 is threaded to the end 33 of the access opening 29. FIG. 19 depicts a sectional view of the body element 12 having a first recess 90 and handle attachment element 92 and a spring receptacle 94. The first recess 90 operates in combination with the handle attachment element 92 to maintain alignment of the push sleeve 16. A second recess can be located on the opposite side of the body element, not shown, forms a mirror image for the handle attachment. The spring receptacle 94 houses springs 32 and 32' illustrated in FIG. 2 providing a spring bias for the movement of the lever handle 14.

Figure 21:
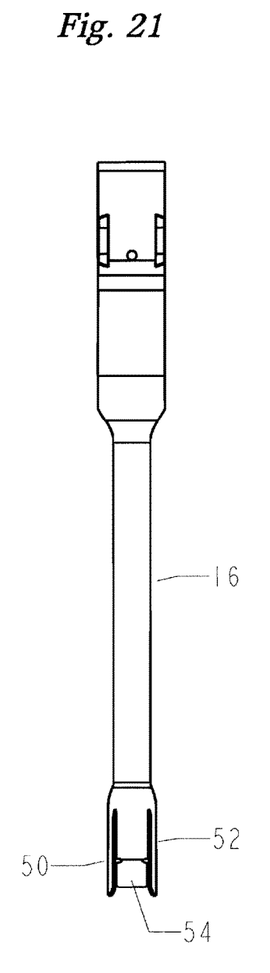
FIG. 21 is an front view of the push sleeve.
Figure 22:
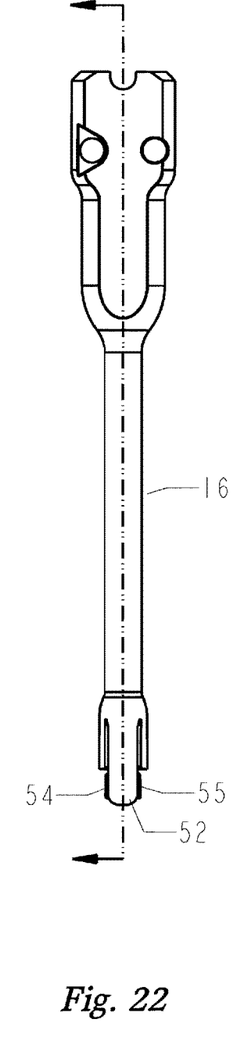
FIG. 22 is a side view of FIG. 21.
Figure 23:
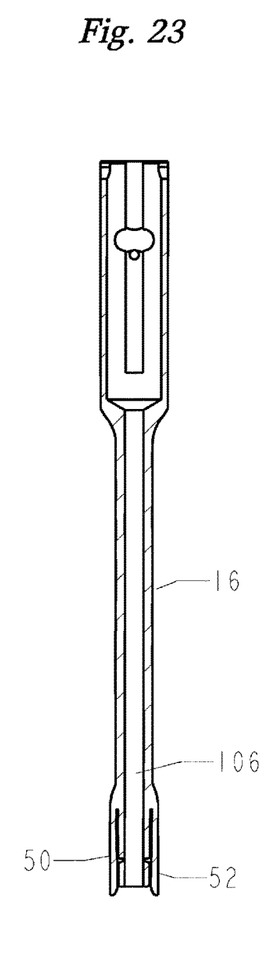
FIG. 23 is a cross-sectional view of FIG. 21.

Referring now to FIGS. 21-23, illustrated is the push sleeve 16 having pinch fingers 50 and 52 abutting the relief areas 54 and 55. Preferably the push sleeve 16 is formed from a single piece of material with the pinch fingers 50 and 52 constructed and arranged to frictionally engage a tulip 80 so as to maintain the tulip 80 in a fixed position during the installation procedure. FIG. 22 is a side view of FIG. 21 depicting the front rest area 54 and the rear rest area 55. The rest areas receive the U-shaped receptacle section 91 of a tulip with the pinch fingers 50 and 52 and is spaced apart from the passageway 106 which extends the longitudinal length of the push sleeve 16 for receipt of the collet tip 20 and expander pin.

Figures 24, 25, 26:
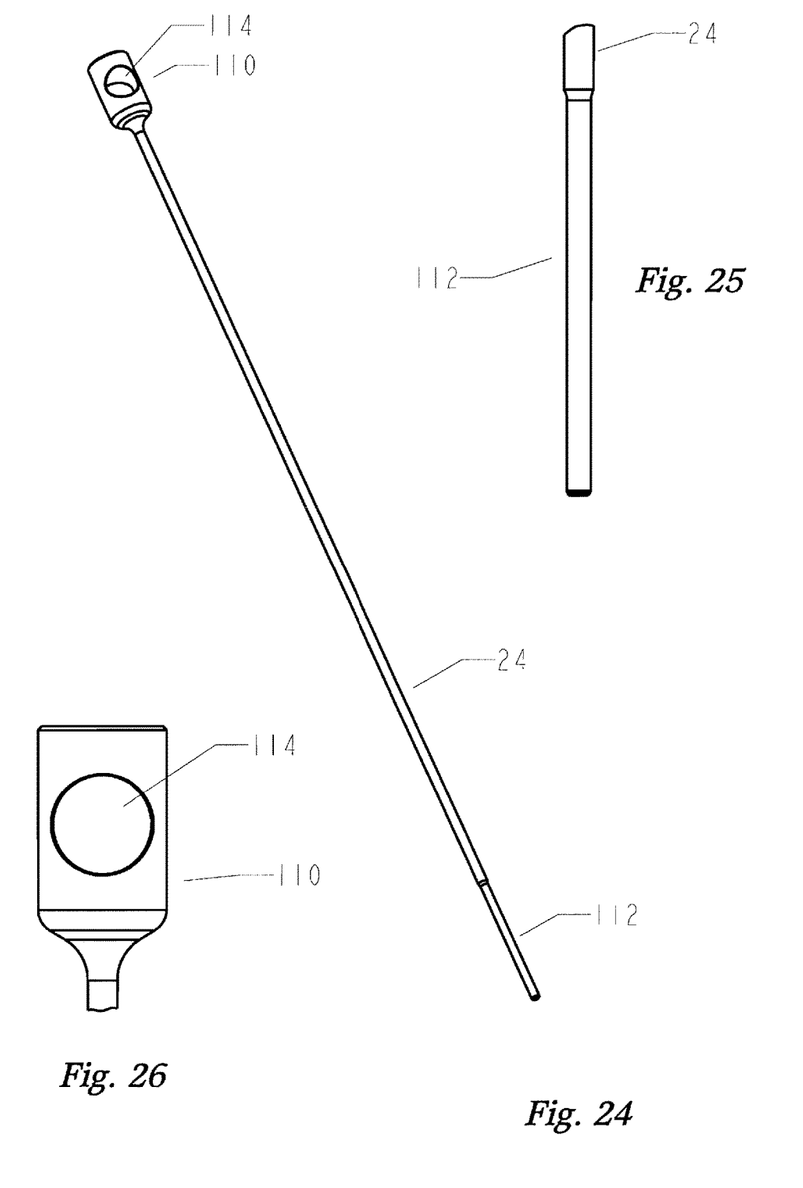
FIG. 24 is a perspective view of the expander pin.
FIG. 25 is a plane view of the expander pin reduced diameter end.
FIG. 26 is a plane view of the expander pin head.

FIG. 24 illustrates the expander pin 24 having a pin head 110 used for expanding the tip of the collet for securing to the bone screw, or retracting the collet tip 20 for detaching the instrument from the bone screw. The expander pin 24 has a distal end with a reduced diameter section 112 which allows for the desired expanding of the collet tip 20 when required. FIG. 25 is an enlarged view of the reduced diameter section 112 allowing for rigidity along the length of the expander pin 24 with only the reduced diameter section 112 used to engage the collet tip 20. FIG. 26 is an enlarged view of the expander pin head 110 having aperture 114 for engagement of a pivot pin 31.

Figure 27:
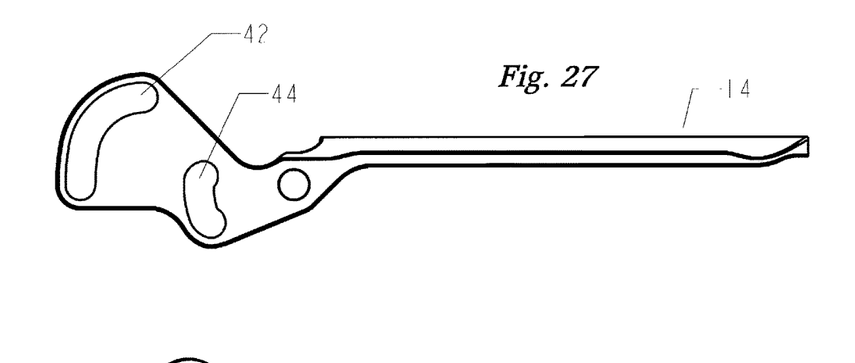
FIG. 27 is a side view of the lever handle.
Figure 28:
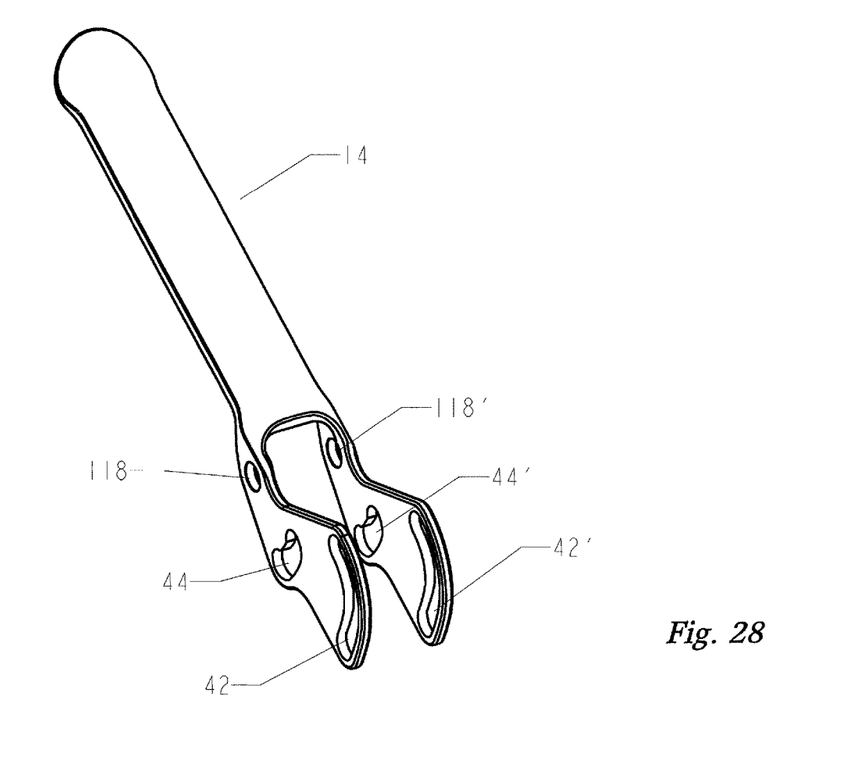
FIG. 28 is an isometric view of the lever handle.
Figure 29:
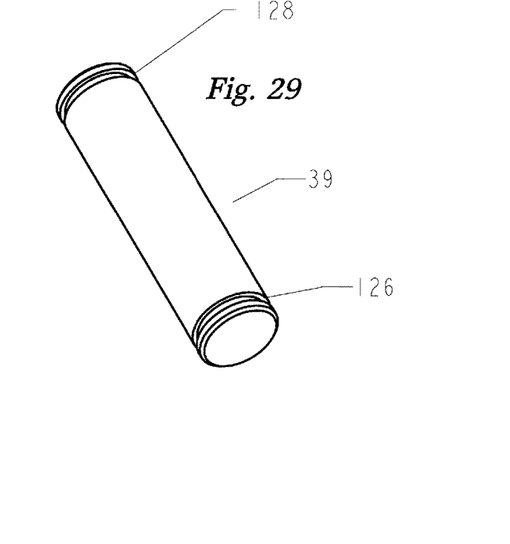
FIG. 29 is an isometric view of a pivot pin.
Figure 30:
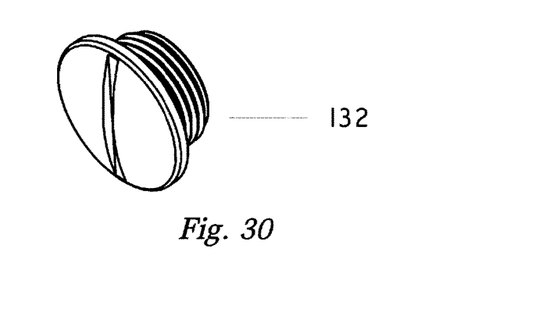
FIG. 30 is a top perspective view of an end cap.
Figure 31:
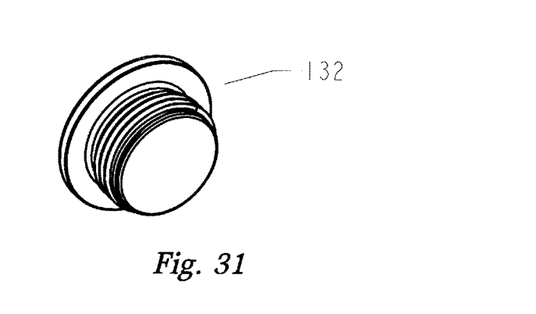
FIG. 31 is a bottom perspective view of the end cap.
Figure 32:
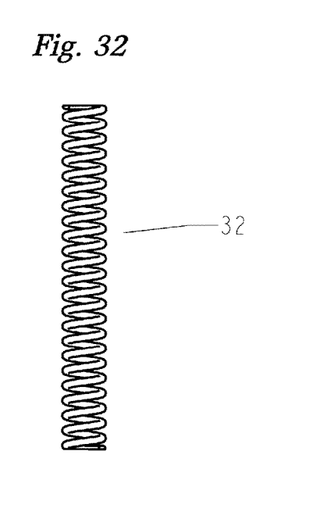
FIG. 32 is a plane view of a compression spring.
Figure 33:
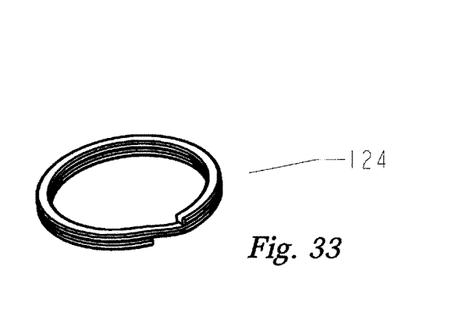
FIG. 33 is an isometric view of a pivot pin retainer ring.

FIGS. 27 through 33 are component parts of the inserter instrument 10. FIG. 27 is a lever handle 14 with cam track 42 for operation of the expander pin 24 and cam track 44 for operation of the push sleeve 16. FIG. 28 is an isometric view of FIG. 27 illustrating the positioning of the cam track 42' for the expander pin and opposing cam track 44' for receipt of an expander pin. The opposing cam track 44' is used in combination with apertures 118 and 118' for receipt of the pivot pin 39 to allow rotation of the lever handle 14. FIG. 29 illustrates pivot pin 39 for insertion into the cam track 44 to engage the expander pin 24. FIG. 30 is the end cap 132, placed on the body element 12 after insertion of the expander pin 24. FIG. 31 is the end cap 132 placed on the body element 12 after insertion of the expander pin 24. FIG. 32 depicts spring 32, the second spring 32' is identical. FIG. 33 is a retainer ring 124 that fits within the grooves 126 and 128 of the pivot pin 39.

Operational steps of the instrument are as follows: First sequence of the inserter instrument 10 is to attach and load the tulip 80 by sliding the U-shaped receptacle 99 of the tulip onto the resting sections 54 and 55 of the end of the push sleeve 16 wherein the pinch fingers 50 and 52 temporarily engage the tulip 80 during the installation steps. The pinch fingers 50 and 52 are machined to create a spring/pinched effect to hold the tulip in place using frictional engagement.

The end of the instrument includes a collet tip 20 capable of collapsing during insertion into an anchored bone screw 60. The collet tip 20 is expanded wherein a lobe 88 on the collet tip 20 is used to engage a relief groove 66 on the bone screw 60. An expander pin 24 is placed in a stand-by position so to allow the insertion of the collet tip 20 into a cavity which houses the relief groove 66 formed in the head of the bone screw 60.

A lever handle 14 is squeezed from 30° to the 25° (5° of motion), the cam track 44 controlling the expander pin 24 wherein the expander pin 24 is placed into a position to prevent the now expanded collet tip 20 from collapsing wherein the instrument tip is locked onto shank.

As the lever handle 14 is squeezed from 25° to the 5° (20° of motion), the cam track 44 pushes the push sleeve onto the shank head to the capture position while the collet tip 20 is being pulled with an equal force but in an opposite direction. The cam for the expander pin 24 is in a 20° of idle position.

As the lever handle 14 is squeezed from a 5° to the 0° (5° of motion—lever handle fully cycled), the cam controlling the collet tip pulls the expander pin 24 back to unblock the collet area. The collet tip 20 can then collapse and the instrument is no longer locked onto the screw. The cam controlling the push sleeve is in 5° of idle. Once completed, the surgeon simply pulls the instrument away from the screw to remove the instrument, and the captured tulip 80 remains attached to the shank head.

Once the tulip, modular head, is assembled to the bone screw, the assembly is no different than a convention pedicle screw assembly which requires a rod component, a set screw component, and a final tightening of the set screw.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An instrument for assembling a tulip onto a bone screw having a relief groove comprising:

a body element having a distal end sized to receive a tulip;
an expandable collet having a lobe positioned within said body element;
an inserter pin positioned within said collet; and
a cam operated by a lever handle for moving said inserter pin from a first position wherein said lobe forms a first diameter to a second position wherein said lobe forms a second diameter that engages the bone screw relief groove, and pushes the tulip onto a bone screw while pulling on said bone screw with equal and cancelling forces.

2. The instrument for assembling a tulip onto a bone screw according to claim 1 wherein said body element includes at least one pinch finger to frictional engage the tulip.

3. The instrument for assembling a tulip onto a bone screw according to claim 2 wherein said body element includes a push sleeve arranged to press against the top of the tulip, said push sleeve including at least one tulip rest area to maintain the tulip in a position as held by said pinch finger.

4. The instrument for assembling a tulip onto a bone screw according to claim 1 including a cam means for securing said collet to the bone screw before pushing the tulip onto the bone screw.

5. The instrument for assembling a tulip onto a bone screw according to claim 1 wherein said lever handle includes a first cam for moving said inserter pin within said collet and a second cam for pushing the tulip onto the bone screw.

6. The instrument for assembling a tulip onto a bone screw according to claim 1 wherein said lever handle includes at least one spring to bias said lever handle in the first position.

7. The instrument for assembling a tulip onto a bone screw according to claim 1 wherein said body element includes a rest area constructed and arrange to receive a U-shape tulip.

8. The instrument for assembling a tulip onto a bone screw according to claim 1 wherein said collet includes spacing to permit said collet to collapse to a first diameter and expand to a second diameter.

* * * * *